United States Patent [19]
Masai et al.

[11] Patent Number: 5,087,449
[45] Date of Patent: Feb. 11, 1992

[54] METHOD FOR THE PREPARATION OF A SUBSTANCE CAPABLE OF PROLIFERATING BIFIDOBACTERIA GROWTH AND THE SUBSTANCE

[75] Inventors: Teruhisa Masai, Kanagawa; Takanobu Shibuta, Tokyo; Yasuyuki Yoshida, Kanagawa; Yohsuke Suzuki, Chiba, all of Japan

[73] Assignee: Calpis Food Industry Co., Ltd., Tokyo, Japan

[21] Appl. No.: 537,664

[22] Filed: Jun. 14, 1990

[30] Foreign Application Priority Data

Jun. 20, 1989 [JP] Japan .................................. 1-155596

[51] Int. Cl.$^5$ ...................... C12N 1/38; A61K 35/78; C07K 3/02; B01D 13/02
[52] U.S. Cl. .................... 424/195.1; 204/182.3; 204/182.6; 426/43; 435/244; 435/252.1; 435/253.6; 530/378; 530/414
[58] Field of Search ................. 204/182.6, 182.3; 435/244, 253.6, 252.1; 530/414, 378; 426/43; 424/195.1

[56] References Cited

U.S. PATENT DOCUMENTS

| 4,482,574 | 11/1984 | Lee | 426/7 |
| 4,549,947 | 10/1985 | Inoue et al. | 204/182.4 |
| 4,902,673 | 2/1990 | Hayakawa et al. | |

FOREIGN PATENT DOCUMENTS

| 55-85390 | 9/1980 | Japan . |
| 56-58491 | 8/1981 | Japan . |
| 59-179064 | 2/1985 | Japan . |

Primary Examiner—Herbert J. Lilling
Attorney, Agent, or Firm—Browdy and Neimark

[57] ABSTRACT

The present invention relates to a method for purification of a bifidobacteria-proliferating substance which comprises treating the extract of soybean or its treated matters or soybean whey or treated solutions thereof with an ultrafiltration membrane, treating with activated carbon and then subjecting to an electrodialysis treatment. The present invention also relates to the thus obtained bifidobacteria-proliferating substance.

12 Claims, 2 Drawing Sheets

METHOD FOR THE PREPARATION OF A SUBSTANCE CAPABLE OF PROLIFERATING BIFIDOBACTERIA GROWTH AND THE SUBSTANCE

BACKGROUND OF THE INVENTION

1. Field of the Invention

The present invention relates to a method for the preparation of a substance capable of proliferating the growth of bacteria belonging to the genus Bifidobacterium, i.e., *bifidobacteria*.

More particularly, the present invention relates to a method for the purification of a bifidobacteria-proliferating substance which is extracted from soybeans.

2. Description of the Prior Art

In general, bifidobacteria are recognized to have a physiological importance for humans. It is considered that bifidobacteria would be particularly effective for protection from intestinal infections, enhancement of immune function, prevention of enteric putrefaction, decomposition of carcinogenic substances, production of vitamins, etc.

In recent years, it has been attempted in the clinical field to orally administer bifidobacteria per se and this is based on the reports that bifidobacteria are effective for treatment of gastrointestinal disorders, hepatic disorders, skin diseases, allergic diseases, diseases caused by microbisme selectionné et substitué, etc. of babies, infants, adults and aged people.

Also for purposes of utilizing the effectiveness of bifidobacteria, bifidobacteria-containing foodstuffs such as cultured milk products, tableted candy, etc. are commercially available.

It is recognized also from a medical viewpoint that formation of bifidobacteria dominant flora in the intestinal tract of not only infants but also adults and senile people would be effective for prophylaxis of diseases and quick recovery from diseases. For this reason, it is desirable to always maintain a high population of bifidobacteria in the intestine.

If it is wished to temporarily increase bifidobacteria, it may be sufficient to consecutively administer bifidobacteria orally. As compared with the count of the living bifidobacteria orally administered, the count of the living bifidobacteria which can reach the intestinal tract is considerably fewer, because bifidobacteria have a low resistance to acids such as gastric acid, bile acid, etc. It is thus difficult to maintain the count of intestinal bifidobacteria on a high level merely by oral administration of bifidobacteria.

It is thus improtant to provide an environment for retaining and proliferating bifidobacteria in the intestine. For this reason, it has been attempted to maintain the count of intestinal bifidobacteria on a high level, by orally administering a bifidobacteria-proliferating substance either alone or in combination with bifidobacteria.

It is known in Japanese Patent Application Laid-Open Nos. 51-142566, 55-85390, etc. that soybean milk is effective for growth of bifidobacteria. However, it is quite unknown what component of soybean milk is effective.

Oligosaccharides such as stachyose, raffinose, etc. which are contained in soybeans are known as sugars capable of proliferating bifidobacteria.

However, even in the case of using these sugars, the effect of proliferating bifidobacteria is still inferior to that of a bifidobacteria-proliferating substance contained in soybean milk.

SUMMARY OF THE INVENTION

As a result of extensive investigations to purify the bifidobacteria-proliferating substance from soybean extract, etc., the present inventors have discovered that the bifidobacteria-proliferating substance can be sufficiently purified to such an extent that the substance is usable for practical purpose, by performing the following 3 steps as continuous essential treatments during the purification:

1. a treatment with an ultrafiltration membrane having a fractional molecular weight range of 20,000 to 100,000;
2. a treatment of the resulting solution with activated carbon; and
3. an electrodialysis treatment of the resulting solution treated with activated carbon.

The present invention has thus come to be accomplished.

DETAILED DESCRIPTION OF THE PREFERRED EMBODIMENTS

Figure 1:
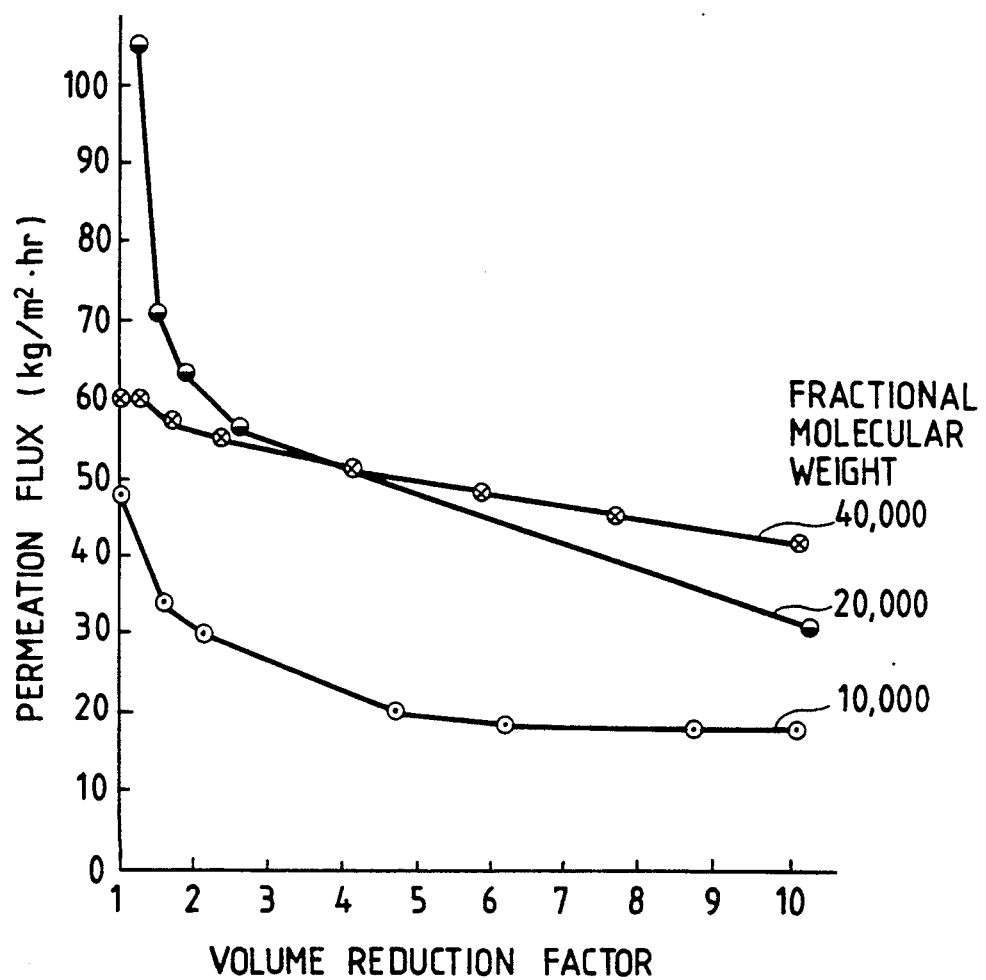
FIG. 1 is a drawing showing the process of treatment of a soybean extract with hot water through an ultrafiltration membrane each having a nominal molecular weight cut-offs of 40,000, 20,000 or 10,000 in Test Example 1.

A great advantage of the present invention in the continous essential 3 steps described above lies in that the co-existing contaminants such as protein, salts, colored materials, etc. can be almost completely separated and the bifidobacteria-proliferating substance can be purified by of such substance from soybean extract or soybean whey to such an extent that the substance is substantially usable for various utilities.

The purification is explained at each step. By the treatment with ultrafiltration membrane with a fractional molecular weight range of 20,000 to 100,000, preferably 40,000 to 60,000, protein, colored materials, microorganisms or the like are separated. There after, in treatment with activated carbon, the remaining 2S protein (S: Svedberg unit) and colored materials are removed by adsorption. The step of adsorbing and removing 2S protein remained even after the ultrafiltration treatment by the activated carbon treatment is one of the characteristic features of the present invention.

Then the electrodialysis treatment follows continuously, whereby desalting is effected and at the same time, charged color substances are removed. In this case, 2S protein is removed from the treated solution by the treatment with activated carbon so that the electrodialysis treatment can be efficiently carried out. Thus, the present invention can provide the method for purification which is extremely advantageous in industry of manufacturing bifidobacteria-proliferating substances.

In the present invention, the electrodialysis treatment can be followed by a treatment with an ion exchange resin. Thus, salts, colored materials, nitrogen compounds and the like which still remain can be completely removed. For the ion exchange resin treatment, it is preferred to pass the solution through a bed of cation resin first and then through a bed of anion resin, and finally a mixed bed of cation and anion resins.

The thus purified bifidobacteria-proliferating substance can be prepared into products suited for various utilities, by concentrating in vacuum to make syrup or by drying to form powder, etc.

In the present invention, as pretreatment of the treatment with ultrafiltration membrane, there may be performed steps of adding calcium chloride to the extract of soybean or the treated matter or soybean whey, heat-treating, adjusting pH to 4.2 to 5.6 and, precipitating and removing protein, salts, etc.

The present invention further includes the bifidobacteria-proliferating substance obtained by treating the extract of soybean or the treated matter or soybean whey with ultrafiltration membrane, treating with activated carbon, subjecting to electrodialysis treatment and then treating with ion exchange resin.

The present invention will be explained below in more detail.

As the raw material used in the present invention, there are extracts of soybean or defatted soybean or their treated matters with water, alcohol, aqueous alcohol solution, etc., soybean whey obtained by defatting and separating protein, and the like. Among them, soybean whey obtainable in large quantities is preferred from the viewpoint of desirable utilization of raw material.

To pretreat the extract of soybean or its treated matters or soybean whey by adding calcium chloride thereto, heating and removing protein, salts or the like is advantageous for smooth operation of the ultrafiltration treatment.

More specifically, impurities are removed by adding 5 to 10 wt % of calcium chloride to the soybean extract or the like based on the solid content (R. Brix value) of the extract, heating to about 80° C. and adjusting pH to 4.2 to 5.6, preferably 4.8 to 5.2 after the temperature was elevated to that level. In this case, decomposition of the product occurs at pH below 4.2 and at pH above 5.6, precipitation of the impurities is not completed.

The extract of soybean or its treated matters or soybean whey or pretreated solutions thereof are subjected to ultrafiltration using a membrane with a fractional molecular weight range of 20,000 to 100,000, preferably 40,000 to 60,000 to collect the filtrates. when the fractional molecular weight is less than 20,000, permeation flow fluxes decrease and bifidobacteria-proliferating substances are lost, resulting in a poor product yield which is not suitable for efficient production. Further when the fractional molecular weight exceeds 100,000, impurities other than the bifidobacteria-proliferating substances are excessive, which require further processing and decrease the efficiency of operation, which is not preferred.

Where the solutions for the treatment with ultrafiltration membrane are treated through the membrane with a fractional molecular weight range of 20,000 to 100,000, preferably 40,000 to 60,000, substances having a molecular weight smaller than the fractional molecular weight are naturally intermingled into the permeated solution. In the case of the soybean extract, soluble proteins having a molecular size of or less than about 2S protein, peptides, charged or non-charged colored organic substances and other organic substances or inorganic substances and the like are mixed into the permeated solution and become interferants in the following purification steps. Therefore, the present inventors have made various investigations and as the result, it has been found that a continuous combination of the ultrafiltration with the activated carbon treatment is effective for removal of protein and colored materials.

It may be sufficient to use commercially available activated carbon as the activated carbon used. The activated carbon treatment can be carried out by adding 0.5 to 5 wt % of activated carbon to the filtrate obtained after ultrafiltration, mixing them and then separating activated carbon by filtration, centrifugal separation, etc.

By the treatment with activated carbon, considerable amounts of protein and colored matters are removed. In particular, the activated carbon treatment is effective for removal of low molecular protein such as 2S protein which is a cause for contaminating the membrane in the subsequent electrodialysis treatment.

The solution treated with activated carbon contains a small quantity of salts. The salts are removed by the following electrodialysis treatment.

In the electrodialysis treatment according to the present invention, the activated carbon treatment is performed as its pretreatment after the treatment with ultrafiltration membrane. Therefore, protein having a small molecular weight, especially 2S protein, is separated and removed, so that the electrodialysis treatment proceeds efficiently.

Although the bifidobacteria-proliferating substance thus obtained by the electrodialysis treatment still contains trace amounts of salts, colored substances, nitrogen compounds, etc., it can be used in various foodstuffs as it is.

In the case of directly using the bifidobacteria-proliferating substance obtained by the electrodialysis treatment for beverage, etc., the trace amount of salts or nitrogen compounds gives a bitter taste and the colored substances injure the color of beverage, which is not preferred.

In the present invention, it is preferred to perform ion exchange resin treatment, after the electrodialysis treatment, in appropriate combination of anionic ion exchange resin, cationic ion exchange resin, etc.

The solution obtained after the electrodialysis treatment or further after the ion exchange resin can be applied to various foodstuffs such as beverage, etc., directly or indirectly, as the bifidobacteria-proliferating substance, in the form of liquid as it is, in the form of syrup obtained by concentration or further in the form of powder obtained by drying (e.g., freeze-drying), etc.

Next, the present invention is described with reference to test examples and examples.

TEST EXAMPLE 1

By extracting 100 kg of whole soybean with 180 liters of hot water at 95° C. for 30 minutes, hot water soybean extract was obtained. Four kg of calcium chloride was added to the extract and its pH was adjusted to 5.0 to remove insoluble matters. The process of treating the thus obtained solution with ultrafiltration membranes having nominal molecular weight cut-offs of 40,000, 20,000 or 10,000 is shown in FIG. 1.

The ordinate shows permeation flux (an amount of permeated liquid which permeates a unit membrane area per unit time ($kg/m^2 \cdot hr$)) and the abscissa shows a volume reduction factor (a value obtained by dividing the initial volume of the supplying solution by a volume of the liquid retained after the treatment; same as a concentration factor).

Using 100 liters of the hot water soybean extract as raw material, a test was carried out using Daicel Multipurpose Tester PCD-40 (manufactured by Daicel Chemical Industries, Ltd.). Liquid temperature of the treating solution, inlet pressure, outlet pressure and amount of circulated flow were 70° C., 8.5 kg/cm$^2$, 5.5 kg/cm$^2$ and 1.2 m$^3$/hrs, respectively.

As is clear from FIG. 1, the permeation flux is small with the nominal molecular weight cut-off of 10,000 and the recovery rate of sugars used as an index of the permeated liquid was not considered practical.

TEST EXAMPLE 2

The hot water soybean extract obtained in Test Example 1 was treated through an ultrafiltration membrane with a fractional molecular weight range of 40,000 and 1% of activated carbon (Taiko Activated Carbon FC-W50, manufactured by Futamura Chemical Industry Co., Ltd.) was added to the permeated liquid. After mixing at 50° C. for 45 minutes, trichloroacetic acid was added to the filtrate to a concentration of 0.1M in the resulting mixture. Observation of the solution reveals that precipitates were formed in the permeated liquid but no precipitates were formed in the liquid which was further treated with activated carbon.

Nitrogen content in each sample was determined in a conventional manner to examine the protein content. The protein content was reduced by the treatment with ultrafiltration membrane and the activated carbon treatment. The results are shown in the following table.

TABLE

| Sample | Protein Content (%) | $\bar{x}$ |
|---|---|---|
| Liquid treated with ultrafiltration membrane | 1.016<br>0.992 | 1.004 |
| Liquid treated with ultrafiltration membrane and treated with activated carbon | 0.7667<br>0.7616 | 0.764 |

TEST EXAMPLE 3

The hot water soybean extract obtained in Test Example 1 was treated with an ultrafiltration membrane with a fractional molecular weight range of 40,000 and 1.5% of activated carbon (Taiko Activated Carbon FC-W50, manufactured by Futamura Chemical Industry Co., Ltd.) was added to the permeated liquid. After mixing at 50° C. for 45 minutes, the color value of the filtrate was observed. A decoloration rate of 80% or more was noted.

The color value is the difference obtained by subtracting absorbancy value at 720 nm from absorbancy value at 500 nm.

The results are shown in the following table.

TABLE

| Sample | | 1 | 2 | 3 | 4 |
|---|---|---|---|---|---|
| Solid content (R. Brix) | | 25.6 | 22.2 | 18.6 | 13.4 |
| Color Value: | prior to treatment | 1.062 | 1.278 | 0.973 | 0.662 |
| 500 nm–720 nm | after treatment | 0.122 | 0.113 | 0.108 | 0.040 |
| Decoloration rate (%) | | 88.5 | 91.2 | 88.9 | 94.0 |

TEST EXAMPLE 4

The activated carbon-treated liquid obtained in Test Example 2 was electrically dialyzed by electrodialysis device Model TS-10-400 (Tokuyama Soda Mfg. Co., Ltd.).

The liquid was treated under a set voltage of 280 V, liquid temperature of 30° C., current of 21 A (at the beginning) to 5.5 A (at the end) for 110 minutes. The desalting rate was 85%.

TEST EXAMPLE 5

The syrup (R. Brix 77°) obtained in Example 1 was freeze dried to give powder. Using the thus obtained bifidobacteria-proliferating substance, raffinose, stachyose and an equimolar mixture of raffinose and stachyose as sugar sources, respectively, the following medium was prepared.

| Bacto-Liver (Difco) extract | 1000 ml |
|---|---|
| Proteose Peptone No. 3 (Difco) | 10 g |
| Trypticase (BBL) | 5 g |
| Yeast Extract (Difco) | 3 g |
| Tween 80 | 1 g |
| Solution B* | 5 ml |
| L-Cystein. HCl.H$_2$O | 0.2 g |
| Sugar source | 10 g |

*10 g of MgSO$_4$.7H$_2$O, 0.5 g of FeSO$_4$.7H$_2$O, 0.5 g of NaCl, 0.337 g of MnSO$_4$ were dissolved in 250 ml of purified water followed by sterilization at 115° C. for 20 minutes.

Each medium was inoculated with 1% of 100-fold dilution of the culture solution of *Bifidobacterium longum* ATCC 15707 in Briggs Liver Broth that was incubated at 37° C. for 24 hours. At the same time, one drop of cysteinascorbic acid solution (2 g of L-cystein HCl.H$_2$O, 34 g of L-ascorbic acid and 11 g of Na$_2$CO$_3$, dissolved in 100 ml of purified water and sterilized at 115° C. for 20 minutes) was added to the medium per 10 ml of the medium followed by incubation at 37° C. for 20 hours.

Turbidity (%) in each medium from 11 hours to 20 hours after the inoculation of culture was measured using integration ball photoelectric scattering photometer Model T-2600D (Tokyo Denshoku Co., Ltd.). The results are shown in FIG. 2.

Figure 2:
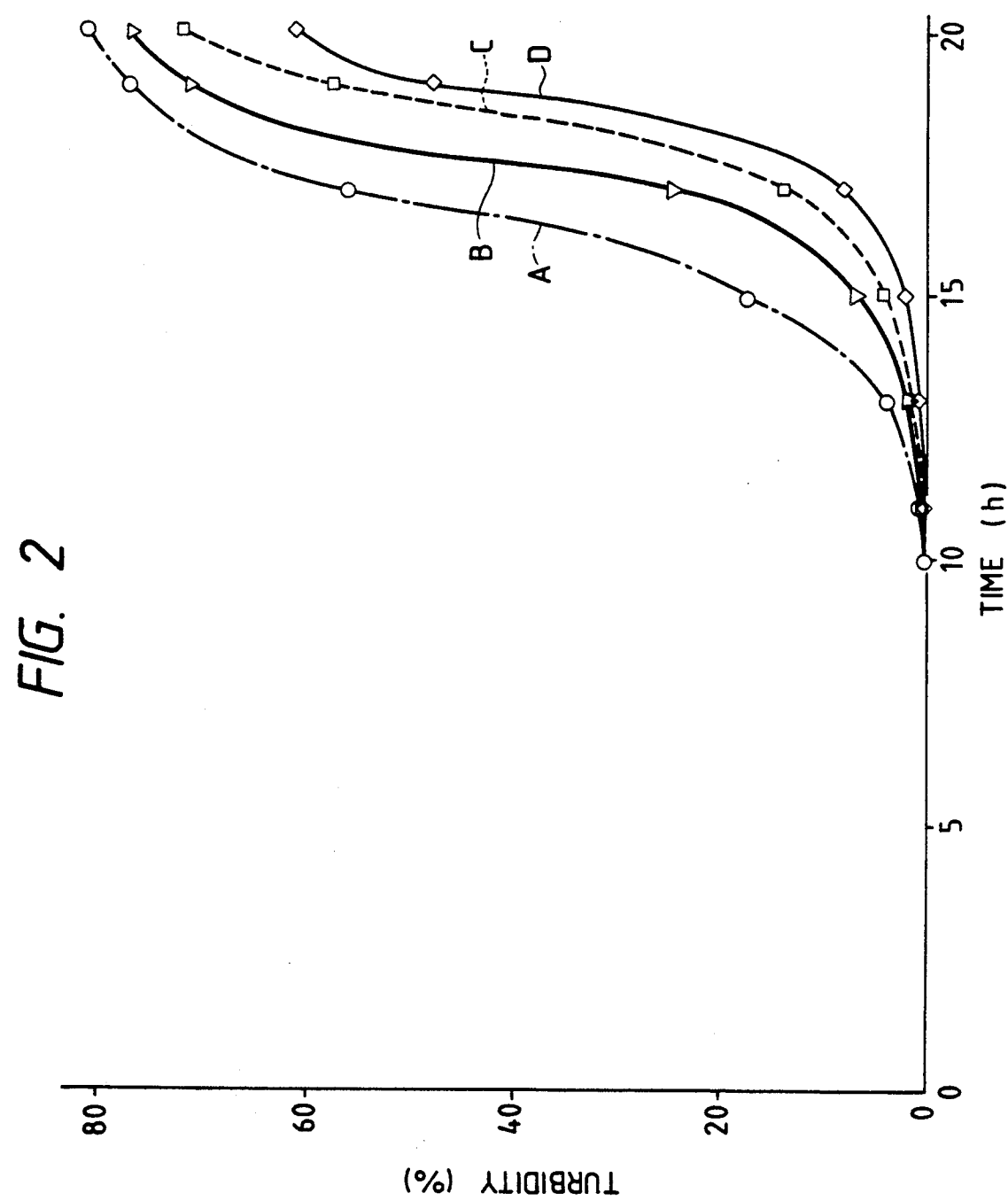
FIG. 2 is a drawing showing the process of culture in Test Example 2 which was determined by comparative culture test of *Bifidobacterium longum* ATCC 15707.

In FIG. 2, A, B, C and D indicate the bifidobacteria-proliferating substance obtained in Example 1, raffinose, stachyose and the equimolar mixture of raffinose and stachyose, respectively.

It is noted from FIG. 2 that the bifidobacteria-proliferating substance of the present invention has the effect of proliferating bifidobacteria.

EXAMPLE 1

After 100 kg of soybean whey (R. Brix 60°) was diluted with 180 kg of water, the dilution was heated to reach 80° C. A solution of calcium chloride (4.5 kg of calcium chloride in 15 kg of water) was added to the dilution in a ratio of 4% to the soybean whey. In the case that pH was outside the range of from 4.8 to 5.0 after the addition, calcium hydroxide was added to adjust the pH to 4.8 to 5.0. After agitation was discontinued, the mixture was held for about 16 hours to separate the supernatant and residue.

The resulting supernatant was subjected to ultrafiltration treatment using an ultrafiltration membrane with a nominal molecular weight cut-off of 40,000, using tubular type module (Daicel DUS-04). The treatment was performed under operating conditions of: inlet pressure of 8 kg/cm$^2$, outlet pressure of 5 kg/cm$^2$, circulating flow amount of 1.5 m$^3$/hr and liquid temperature of 70° C. to give 90% of the stock treating liquid as the liquid permeated through the ultrafiltration membrane (UF permeated liquid).

To the UF permeated liquid was added 2% of activated carbon powder (manufactured by Futamura Chemical Industry Co., Ltd., FC-W50) to contact with each other at 30° to 50° C. for about an hour. Then, filtration was carried out using a filter press.

Then, using an electrodialysis device (manufactured by Tokuyama Soda Mfg. Co., Ltd., Model TS-2), electrodialysis was performed. That is, ion exchange membrane composed of 10 pairs of 2 dm$^2$ each of anionic membrane and cationic membrane was used. Desalting was carried out under operating conditions of: initial voltages of 14 V, initial current of 9.4 A, final voltages of 9.4 V, final current of 1.56 A, and liquid temperature of 30° to 50° C., until the electric conductivity of the liquid reached 3 mS/cm.

The electrodialysis treated liquid was cooled to 10° C. or below followed by ion exchange treatment. The liquid was passed through cation-bed (Diaion PK216, 35 liters), anion-bed (Diaion WA30, 35 liters), mixed bed (Diaion PK216, 5 liters and Diaion PA408, 10 liters), in this order, to give the ion exchanged liquid.

The thus treated liquid was concentrated in vacuum to give about 30 kg of the bifidobacteria-proliferating substance having the composition shown in the following table as syrup.

TABLE

| Water | 24.0% |
|---|---|
| Protein | 0.2% |
| Lipid | 0% |
| Fiber | 0% |
| Ash | 0.1% |
| Sugar | 75.7% |
| Total | 100 |

While the invention has been described in detail and with reference to specific embodiments thereof, it is apparent to one skilled in the art that various changes and modifications can be made therein without departing from the spirit and the scope of the present invention.

What is claimed is:

1. A method for purification of a substance for assisting bifidobacteria growth which comprises subjecting the extract of soybean or its treated matters or soybean whey or treated liquid thereof to ultrafiltration membrane with a fractional molecular weight of at least about 20,000 and activated carbon treatments and then desalting by an electrodialysis treatment.

2. A method for purification of a substance for assisting bifidobacteria growth according to claim 1 which further comprises an ion exchange resin treatment.

3. A method for purification of a substance for assisting bifidobacteria growth as claimed in claim 1, wherein said ultrafiltration membrane used for the ultrafiltration membrane treatment is an ultrafiltration membrane with a fractional molecular weight in the range of 20,000 to 100,000.

4. A method for purification of a substance for assisting bifidobacteria growth as claimed in claim 1, wherein, as a pretreatment of said ultrafiltration membrane treatment, the extract of soybean or its treated matters or soybean whey or treated liquid thereof is treated by addition of calcium chloride, the mixture being heated and pH being adjusted to 4.2 to 5.6.

5. A method according to claim 1, wherein said activated carbon treatment is carried out after said ultrafiltration membrane treatment.

6. A method according to claim 2, wherein said activated carbon treatment is carried out after said ultrafiltration membrane treatment.

7. A method according to claim 3, wherein said activated carbon treatment is carried out after said ultrafiltration membrane treatment.

8. A method according to claim 4, wherein said activated carbon treatment is carried out after said ultrafiltration membrane treatment.

9. A method for purification of a substance for assisting bifidobacteria growth as claimed in claim 2, wherein said ultrafiltration membrane used for the ultrafiltration membrane treatment is an ultrafiltration membrane with a fractional molecular weight in the range of 20,000 to 100,000.

10. A method for purification of a substance for assisting bifidobacteria growth as claimed in claim 2, wherein as a pretreatment of said ultrafiltration membrane treatment, the extract of soybean or its treated matters or soybean whey or treated liquid thereof is treated by addition of calcium chloride, the mixture being heated and pH being adjusted to 4.2 to 5.6.

11. A method for purification of a substance for assisting bifidobacteria growth as claimed in claim 1, wherein said ultrafiltration membrane used for the ultrafiltration membrane treatment is an ultrafiltration membrane with a fractional molecular weight in the range of 40,000 to 60,000.

12. A method for purification of a substance for assisting bifidobacteria growth as claimed in claim 2, wherein said ultrafiltration membrane used for the ultrafiltration membrane treatment is an ultrafiltration membrane with a fractional molecular weight in the range of 20,000 to 100,000.

* * * * *